(12) United States Patent
Hardman et al.

(10) Patent No.: US 10,024,811 B2
(45) Date of Patent: *Jul. 17, 2018

(54) XRF INSTRUMENT WITH REMOVABLY ATTACHED WINDOW PROTECTING FILM ASSEMBLY

(71) Applicants: Peter Hardman, Woburn, MA (US); Fabrice Cancre, Lexington, MA (US)

(72) Inventors: Peter Hardman, Woburn, MA (US); Fabrice Cancre, Lexington, MA (US)

(73) Assignee: Olympus Scientific Solutions Americas Inc., Waltham, MA (US)

( * ) Notice: Subject to any disclaimer, the term of this patent is extended or adjusted under 35 U.S.C. 154(b) by 236 days.

This patent is subject to a terminal disclaimer.

(21) Appl. No.: 15/157,009

(22) Filed: May 17, 2016

(65) Prior Publication Data

US 2016/0258888 A1 Sep. 8, 2016

Related U.S. Application Data

(63) Continuation-in-part of application No. 14/249,857, filed on Apr. 10, 2014, now Pat. No. 9,372,164.

(51) Int. Cl.
*G01N 23/223* (2006.01)

(52) U.S. Cl.
CPC ..... *G01N 23/223* (2013.01); *G01N 2223/301* (2013.01); *G01N 2223/317* (2013.01); *G01N 2223/318* (2013.01)

(58) Field of Classification Search
CPC .. G01N 23/223; G01N 2223/076; G21K 1/06; A61B 6/485; A61B 6/10; A61B 6/102; A61B 6/107; A61B 6/582; A61B 6/585; H01J 5/18; H01J 35/18; G03F 7/70808

USPC ............. 378/44, 45, 161, 204, 207
See application file for complete search history.

(56) References Cited

U.S. PATENT DOCUMENTS

| 6,965,118 | B2 | 11/2005 | Martin et al. |
| 7,375,358 | B1 | 5/2008 | Martin et al. |
| 7,375,359 | B1 | 5/2008 | Grodzins |
| 7,430,274 | B2 | 9/2008 | Connors et al. |
| 7,671,350 | B2 | 3/2010 | Grodzins |
| 8,989,354 | B2 * | 3/2015 | Davis ............... H01J 35/18 378/161 |

(Continued)

FOREIGN PATENT DOCUMENTS

WO 00/37928 6/2000

*Primary Examiner* — Jurie Yun
(74) *Attorney, Agent, or Firm* — C. Tricia Liu; Robert Kaim

(57) ABSTRACT

Herein disclosed is an x-ray florescence (XRF) test system which comprises an XRF test instrument used for testing a test target's responses to X-rays, the instrument including a test window allowing the X-ray and its responsive energy to pass through, and a window protecting film assembly allowing X-rays to pass through and providing protection to the window, the film assembly being configured to be coupled with the window in a fashion to be removed from or applied or reapplied over the window. The corresponding calibration mode can be manually or automatically applied according to the specific film assembly presently in use. An embodiment of the film assembly comprises a thin film fixed with an adhesive layer to a supporting frame having a closely spaced array of apertures.

14 Claims, 8 Drawing Sheets

(56) References Cited

U.S. PATENT DOCUMENTS

| | | |
|---|---|---|
| 9,176,080 B2 | 11/2015 | Drummy |
| 9,372,164 B2 * | 6/2016 | Cancre ................. G01N 23/223 |
| 2008/0152079 A1 | 6/2008 | Tannian et al. |

* cited by examiner

XRF INSTRUMENT WITH REMOVABLY ATTACHED WINDOW PROTECTING FILM ASSEMBLY

RELATED APPLICATIONS

This application is a continuation-in-part of U.S. Non-Provisional application entitled "AN XRF INSTRUMENT WITH REMOVABLY ATTACHED WINDOW PROTECTING FILMS", application Ser. No. 14/249,857, filed Apr. 10, 2014, and incorporated herein by this reference.

BACKGROUND OF THE INVENTION

In X-ray fluorescence (XRF) testing, portable testing instruments are often subject to harsh environment. The instrument test windows often need to be protected from possible dusting, intrusion and abrasion from the test material.

However, applying protecting material to the test window often impedes the accuracy and sensitivity of the test result, particularly for testing elements with low atomic numbers.

For example, polyethylene or polyimide is often used material for window shields or a cover. Polyethylene is more transparent and therefore less of absorbing to low energy X-rays than polyimide, but is not as resistant to punctures.

It is therefore desirable to have the sensitivity that polyethylene yields for elements with lower atomic numbers, and with the same instrument to have the physical protection offered by thicker polyimide when the testing requirement for sensitivity is not as demanding, such as for testing Titanium (Ti) or other higher atomic numbers. It provides many benefits for an instrument to be equipped with a layer of window guard or protecting film that can be easily applied on or taken off for testing elements with higher or lower atomic numbers, respectively.

Various shields and/or window guards have been seen in existing practice designed for X-ray devices such as handheld X-ray fluorescence (XRF) instruments. Examples include U.S. patent Ser. No. 13/551,232; U.S. Pat. Nos. 7,430,274; 7,375,359; 7,375,358; 6,965,118; and 7,671,350, as well as WO 00/37928, are all incorporated herein by this reference. See also U.S. Published Application No. US-2008-0152079. However, none of these background arts have been seen to provide the simple, low cost and convenient solution as described herein in the present disclosure.

SUMMARY OF THE INVENTION

The fragile sealing window used in an X-ray analytical instrument can be protected from encounters with foreign objects by applying the protection film with embodiments of the present disclosure.

It is a general object of the present disclosure to overcome the problems associated with the background art by introducing an economical, simple, easy-to-apply and re-attachable window guard that engages whenever: a) a measurement mode is for testing heavier elements, b) a penetrating object is sensed to be in close proximity to the detector sealing window during a measurement mode, c) the instrument is not in usage, or d) determined by the operator to apply, etc.

The foregoing and other objects of the present disclosure may be realized with a replaceable protective film that covers the detector window, and can be removed and reapplied.

In accordance with various embodiments of the invention, the protective covering or guard film may be attached on top of the detector window by adhesive means, or taken off and re-attached to the window depending on the need of the operation of the instrument. Other means of attaching, removing and re-attaching can include using other coupling means, such as magnetic coupling, thread screw coupling, etc.

In an embodiment of the invention, a thin guard film may be attached by adhesive means to a robust frame for supporting the thin film, and the frame may have a closely spaced pattern of apertures providing maximum support for the thin film while presenting minimum obstruction to the passage of X-rays.

Other features and advantages of the present invention will become apparent from the following description of the invention which refers to the accompanying drawings.

BRIEF DESCRIPTION OF THE DRAWINGS

The drawings presented are not necessarily to scale. Emphasis is placed upon illustrating the principles of the preferred embodiment of the method.

DETAILED DESCRIPTION OF THE PREFERRED EMBODIMENT

The method proposed by the preferred embodiment is herein presented by referring to FIGS. 1-5c.

Figure 1:
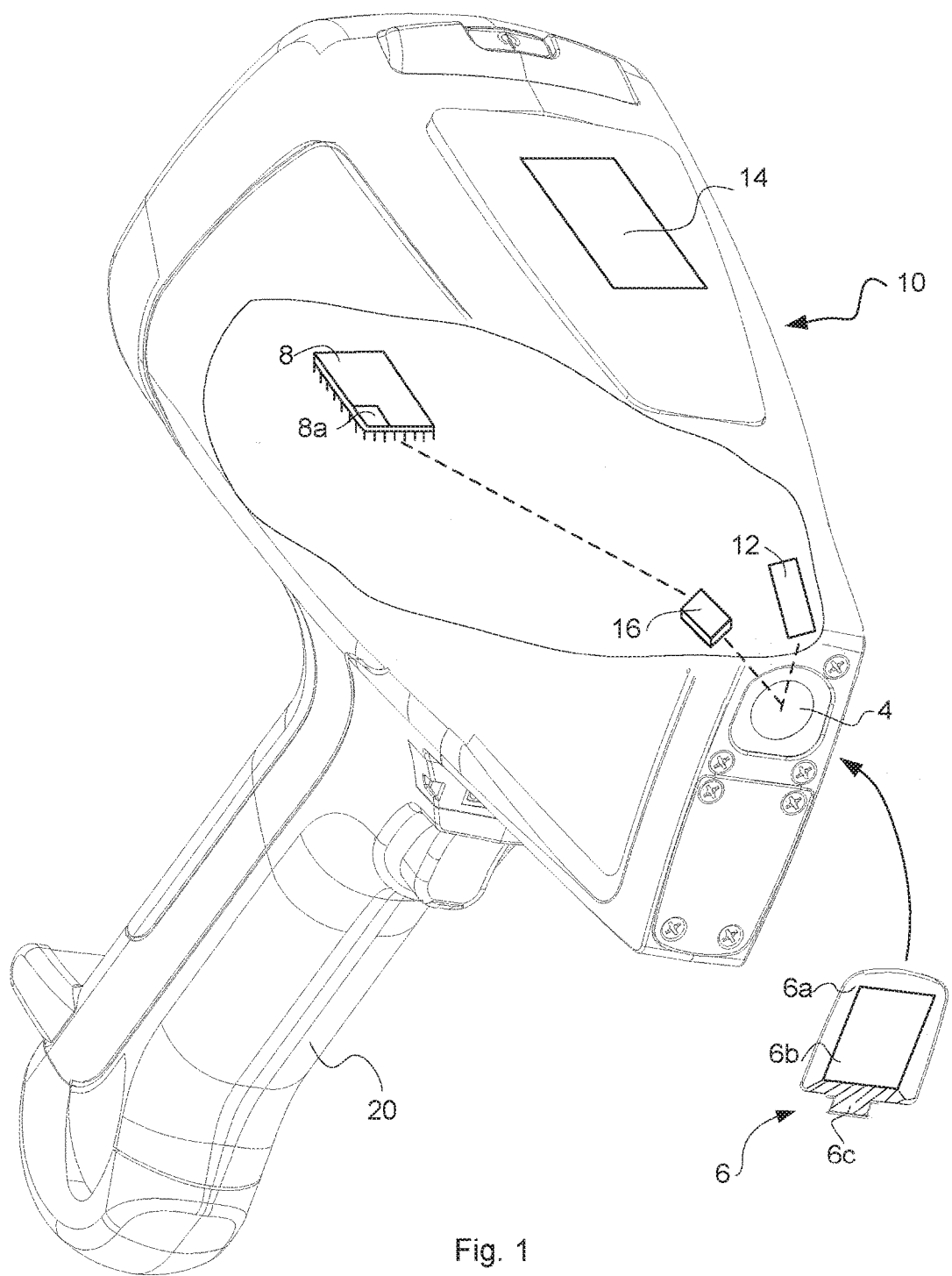
FIG. 1 is a schematic of an XRF instrument with a removable protective film ready to be applying over the window of the XRF instrument according to the present disclosure.

As seen in FIG. 1, a conceptual view of an XRF instrument 10 is configured to couple with a plurality of protection films 6, one at a time during operation. A test window 4 is devised as in conventional XRF instruments. An important novel aspect of the solution herein presented includes the employment of a plurality of removable protection films 6, with which any number can be applied over a test window 4 according to the present invention.

The XRF instrument further optionally includes an X-ray source 12, a detector 16, a data processor 8 and a display 14, largely in the same way as conventional XRF instruments.

An immediate exemplary usage of such embodiment is to affix the commonly used polyethylene film or coating to window 4 in a non-removable fashion as conventionally done in some XRF instruments. The sensitivity that polyethylene yields for elements with lower atomic numbers is desirable for testing samples with lower atomic numbers.

Therefore, no additional removable film or guard 6 is needed for such situation. However, with the same instrument 10, in order to achieve the physical protection needed for many testing environments, thicker polyimide removable film 6, such as polyimide 75 μm, can be applied over the existing non-removable polyethylene film or coating. This is the most desirable when the testing requirement for sensitivity is not as demanding, such as testing for Titanium (Ti) or other higher atomic numbers.

Figure 2:
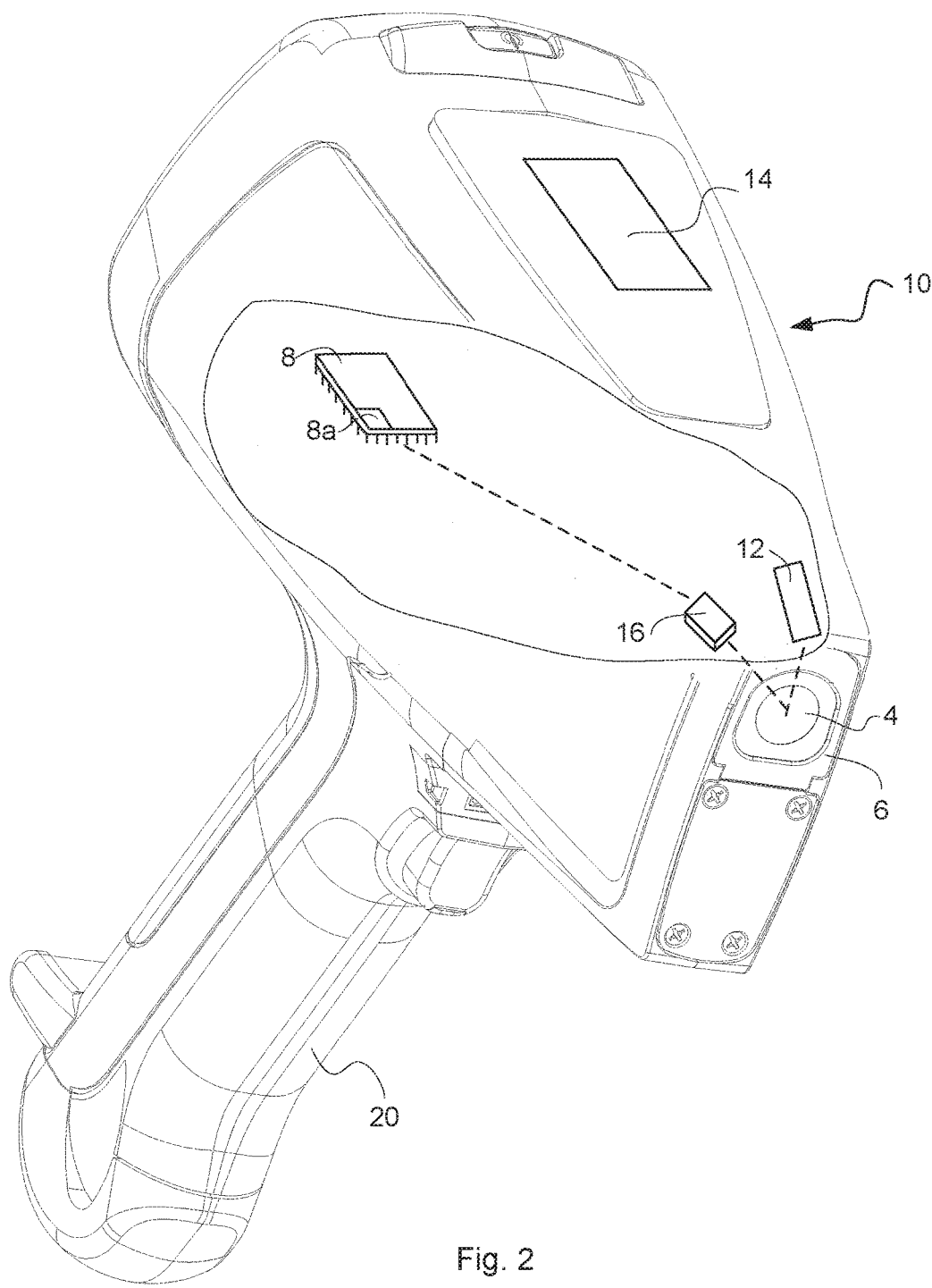
FIG. 2 is a schematic of the XRF instrument in FIG. 1 with the removable protective film applied over the window.

It should be appreciated that the usage of any number of, and any combination of any kinds of films, collectively numerated as 6 in FIGS. 1 and 2 should be determined by the testing specifics, and the usage of all such should be within the scope of the present disclosure.

For example, the fixed layer of film is optional, and it doesn't have to be polyethylene. Polyimide with 25 μm is another often used film that can be used as the fixed layer. The removable film 6 can be also many choices.

Reference is still made to FIG. 1. Removable film 6 is preferably attached over window 4 by using a removable attaching means. Accordingly, film 6 is shown to be configured to include an adhesive backing 6a encircling the edge of film 6. Alternatively, the adhesive backing 6a can be applied in sections, instead of continuously encircling the edge.

Continuing to refer to FIG. 1, film 6 can optionally have an extruded tab 6c allowing easy application onto and removal from window area 4. Preferably, working area 6b should be left clean from adhesives and human touch.

It should be appreciated that removable film 6, adhesive backing 6a, tab 6c and working area 6b each and all can take any shape to suit for specific XRF instruments, and any such shape used by a removable film falls within the scope of the present invention.

It should also be appreciated that the adhesive material (not shown) applied to backing 6a can be of any material suited for the purpose of attaching film 6 in a removable manner.

Referring to FIG. 2, XRF instrument 10 is conceptually shown when removable film 6 is applied onto window 4.

Figure 3:
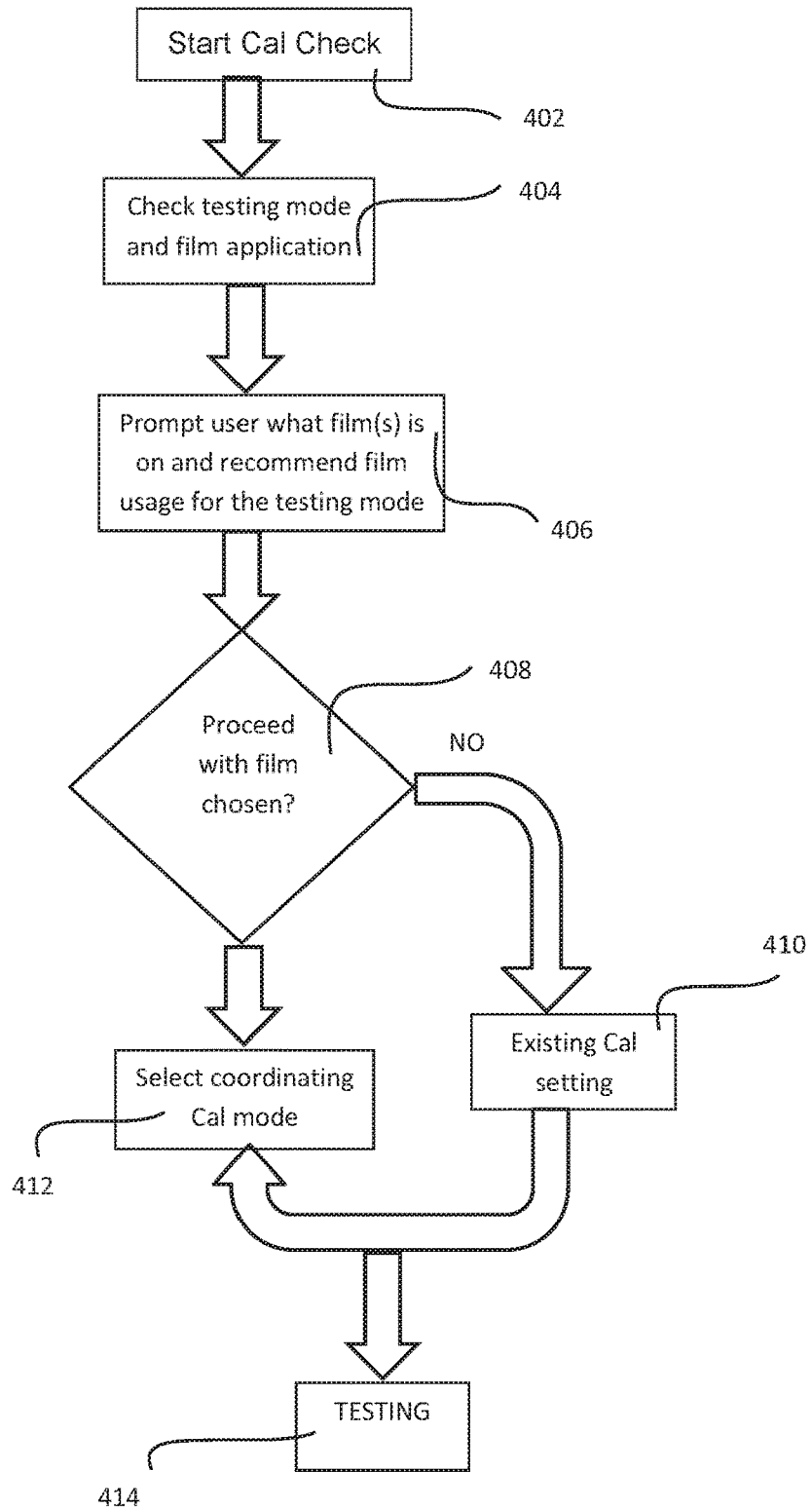
FIG. 3 is a flowchart of the process for operating the XRF instrument accommodating the application of the protective film.

Reference is now primarily made to FIG. 3 with continued reference to FIG. 1. FIG. 3 is a flowchart showing an operational procedure related to the usage of the embodiment shown in FIG. 1.

In order to accommodate the usage of a plurality of removable films according to the present invention, instrument 10 is preferably devised with a plurality of corresponding calibration modes, preloaded onto processor 8.

It should be noted that the different calibration modes for different types of removable films 6 can be either designed in a new XRF instrument, or achieved by modifying an existing calibration module or functional block residing on the processor of an existing XRF product. The modified calibration module is shown in FIG. 1 as 8a. It can also alternatively be calibrated in a field operation or in a manufacturing set up, all of which should be within the scope of the present invention.

The method of calibrating an XRF instrument for a specific window protection is commonly known. Different calibration modes can be achieved in manufacturing settings for different types of the protection films/guards.

Alternatively, if the quality and thickness of the protecting films are substantially homogenous and standard, one can populate the values of different calibration modes by calculating the energy-dependent effect on the spectrum caused by the corresponding film. One can conduct sufficient number of calibration runs for a specific protecting film, which yield a calibration factor for the film by comparing to the energy reading of the same instrument without the film applied on the same set of samples. With the standard calibration factors established, using the example film Kapton 25 for element Mo testing, one can use the calibration factor associated with this specific protecting film to calculate the new calibration value with the protection film/guard based on normally known calibration values without the protection film. The result specific to this calibration mode for Kapton 25 for Mo testing can be stored in a memory (not shown) of the instrument. The following table shows an exemplary result of such calculation of the calibration mode.

TABLE 1

Calculating Calibration Values for Mo Testing with Kapton 25 as Window Guard

|  | Fe Region | Cu Region | Mo Region |
|---|---|---|---|
| Normal Calibration values | 54.8815 | 85.9407 | 176244 |
| Calibration Factor for film Kapton 25 | 0.9119102 | 0.98551094 | 0.97156215 |
| Calculated Calibration Values with WG | 50.047 | 84.6955 | 171232 |

It can be understood by those skilled in the art that, wherein in Table 1, the content in the top row denotes to "energy regions" associated with known elements in a known sample. "Normal Calibration values" denote the x-ray counts per second from the standard sample without the window guard or the film. "Calculated Calibration Values with WG" denote the x-ray counts per second from the same standard sample, with the window guard or the film.

Yet another note on the calibration modes is that it is preferable to prepare all possible calibration modes with corresponding calibration values for all possible combinations of using, or without using, any and any number of protection films provided with the instrument.

Continuing with FIG. 3, the calibration procedure is preferably made in a form executable functional code, and as a module herein named "film calibration module" 8a shown in FIG. 1. The calibration procedure preferably includes steps as follows.

In step 402, the operator starts testing by starting a "Cal check" with a calibration mode mostly used for a previous session of testing. i.e., light element or heavy atomic element. "Cal check" is commonly referred in XRF as shooting a sample of known elemental composition;

In step 404, calibration module 8a checks the film application to determine whether film is applied, and optionally to determine automatically what kind of film is applied on window 4.

Alternatively, when the known kind of element for testing, such as Mo, is provided to the instrument, module 8a can be configured to determine if the detected film 6 is the right match for such testing.

It should be understood that alternative step 404 can be that the calibration module 8a only checks if film 6 is applied or not, and prompts the operator to check if film 6 is the intended kind of film to be attached.

It can be understood by those skilled in the art that after the Cal Check is initiated at step 402, the energy reading on a known sample can indicate if a protection film is applied. And by comparing the known calibration factors stored in the instrument, such as that listed in Table-1, optionally the calibration module 8a can yield what kind of film is presently attached to the window. Further alternatively, the calibration module 8a can also yield what kind of film is presently attached to the window by comparing the ratios of a couple of know spectrum to a predetermined threshold of such ratios.

In step 406, calibration module 8a mostly via display 14 prompts operator whether film is applied and what kind of film is applied on window 4, and suggests the operator whether to change or remove film or alternatively change the calibration mode.

In step 408, module 8a further checks what film or no film is chosen by the operator. If a specific film is chosen, the procedure moves onto step 412. If no film is chosen, the procedure moves onto step 410.

In step 412, a specific calibration mode suited for the chosen film is chosen by the calibration module, and executed to calibration instrument 10. Alternatively, the operator can also choose the calibration mode via display 14.

In step 410, if the operator determines not to use any protection film and remove the same, the existing calibration mode for window 4 without additional re-attachable protection film 6 is executed to calibrate instrument 10. In the exemplary case shown in Table-1, the row of values of "Normal Calibration Values" is used.

In step 412, instrument 10 is ready for testing.

Figure 4A:
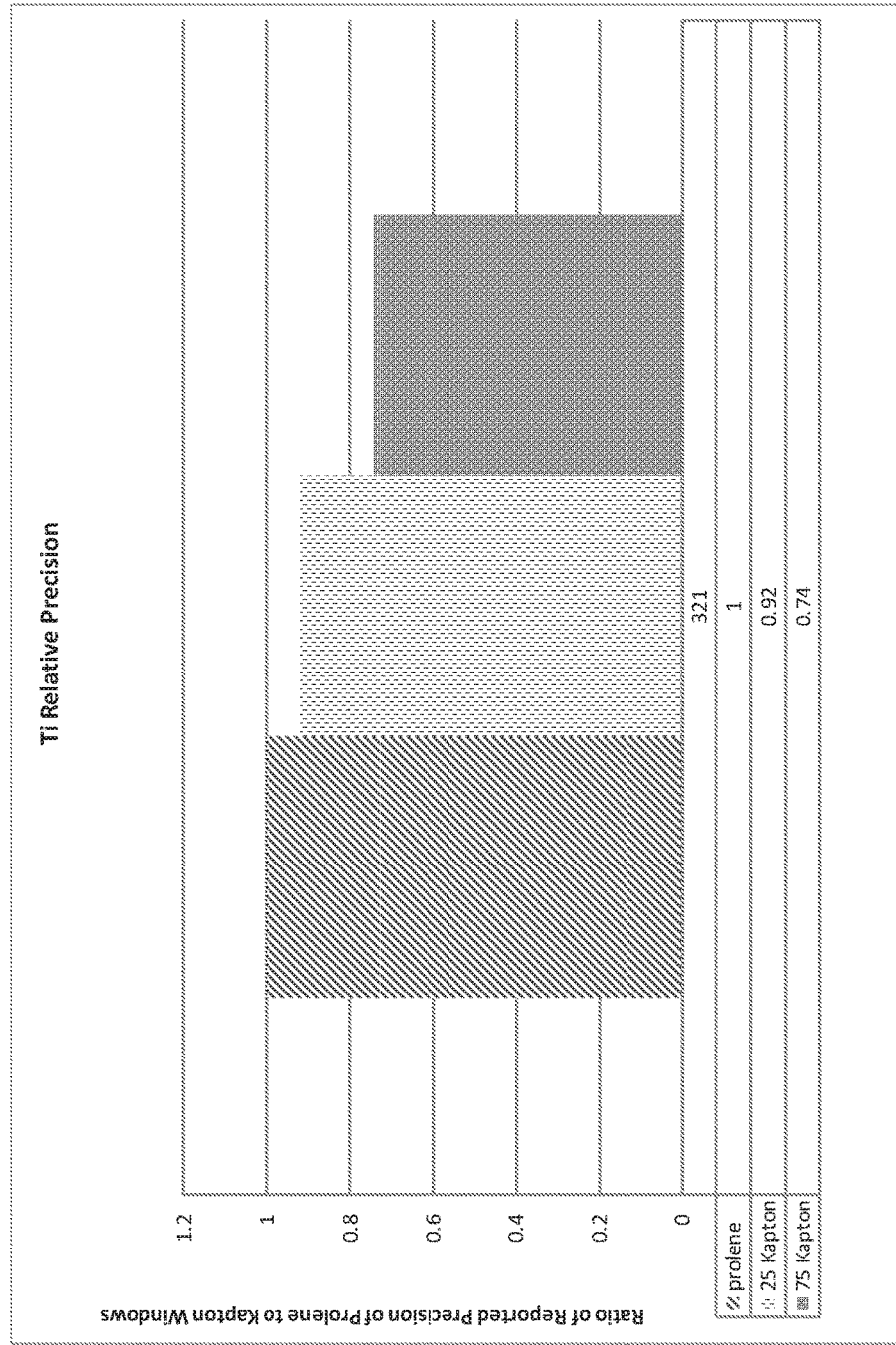
FIGS. 4a and 4b exhibit the effect of the protective films on different XRF measurements, made for light elements and heavy elements respectively.
Figure 4B:
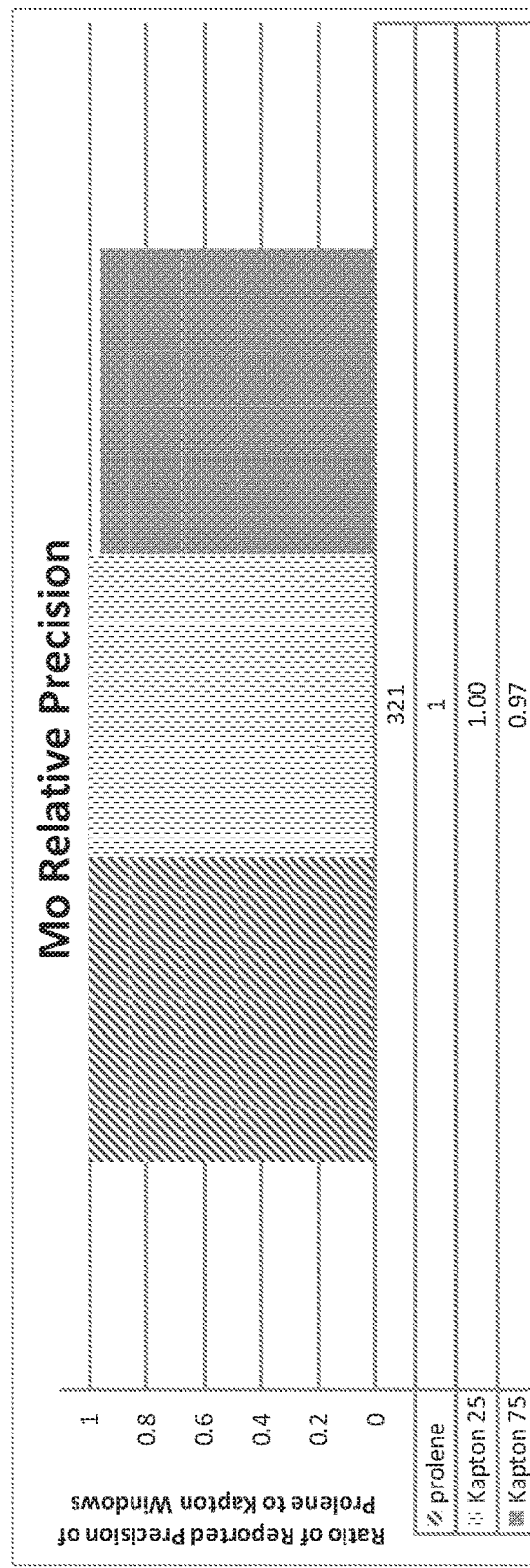

Reference is now made to FIGS. 4a and 4b, whereby two exhibitions are shown for the effect of adding removable films, presented as "ratio of precision of Prolene window", with Prolene (an example of a polyethylene window) exemplarily used as the fixed window base for cases. A Ti element of the lighter end of heavy atomic elements and a Mo element of the heavy atomic elements are used in FIGS. 4a and 4b, respectively. Both elements are tested within Alloy 321 for both cases. In addition, removable films Kapton 25 (an example of a polyimide window) and Kapton 75 are representatively used to compare their respective effectiveness against a fixed window with Prolene.

As can be seen in FIG. 4a that the lighter end of the heavier atomic elements (e.g. Ti) is affected the most by the effect of changing or adding removable films.

As can be seen in FIG. 4b that higher end of heavier atomic elements, such as Mo, is not as affected by adding removable films. Therefore, adding removable films for extra protection is desirable.

The comparison of FIGS. 4a and 4b indicates the benefit of versatility allowing adding or removing protection films to the text window of the XRF instruments.

Figure 5A:
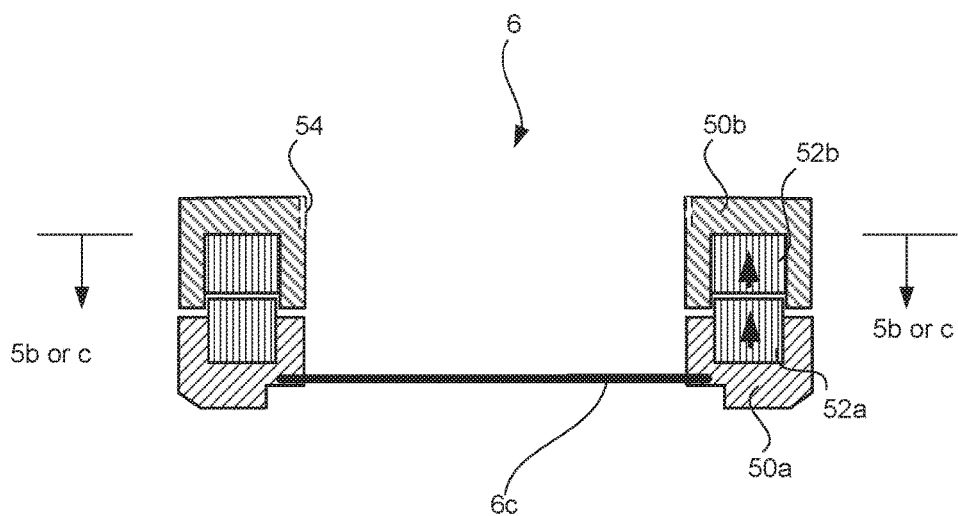
FIGS. 5a, 5b and 5c exhibit another means of attaching and re-attaching the protective film by using magnets as couplings.
Figures 5B, 5C:
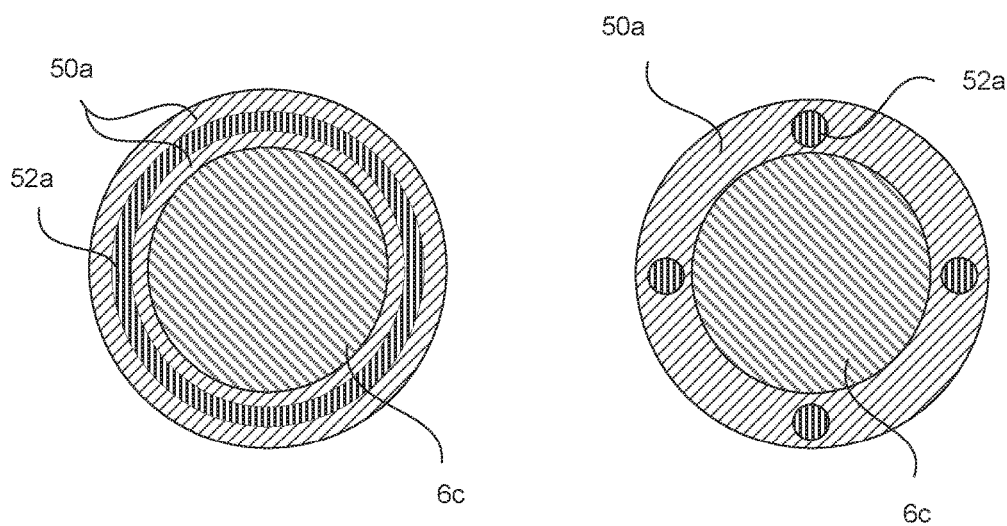

Reference is now made to FIGS. 5a, 5b and 5c, which exhibit an alternative means of attaching and re-attaching the protection film 6. In this alternative attaching method, magnetic attraction force is used to stick or attach the film onto the window of the XRF instrument.

As seen in FIGS. 5a, 5b and 5c, the re-attachable film 6 with magnetic coupling comprises protection film main body 6c, a first holder 50a holding film 6c and one set of magnets 52a, a second holder 50b holding a second set of magnets 52b. As shown in FIG. 5a, it can be appreciated that holder 50b is placed along a window periphery immediately outside and surrounding the window and corresponding matching magnetic coupling 52a in positions. It should be noted that elements 52a and 50b can each be any of the permanent magnets or ferromagnetic material as long as 52a and 52b forms a magnet coupling strong enough to hold the film onto the window. Magnetic couplings 52a and 52b can also be in the forms of whole piece, such as shown in FIG. 5b, or of discrete discs, such as shown in FIG. 5c, that are configured to exert magnetic force on its corresponding counter-parts.

There can be optional attaching means such as a screw thread 54 for the second holder 50b to be attached to window 4, with the corresponding coupling thread on window 4 (not shown). It should be understood by those skilled in the art that other attaching means can be used instead to thread the attached to the second holder 50b to the window.

It can be understood that this alternative magnetic coupling provides a similar advantage as that of adhesive coupling, and that it is simple and convenient for the operator to attach and re-attach the protection film onto or from the window.

It should be appreciated that any other means of attaching and re-attaching, and the associated usage of corresponding calibration modes, should all be within the scope of the present disclosure.

Figure 6:
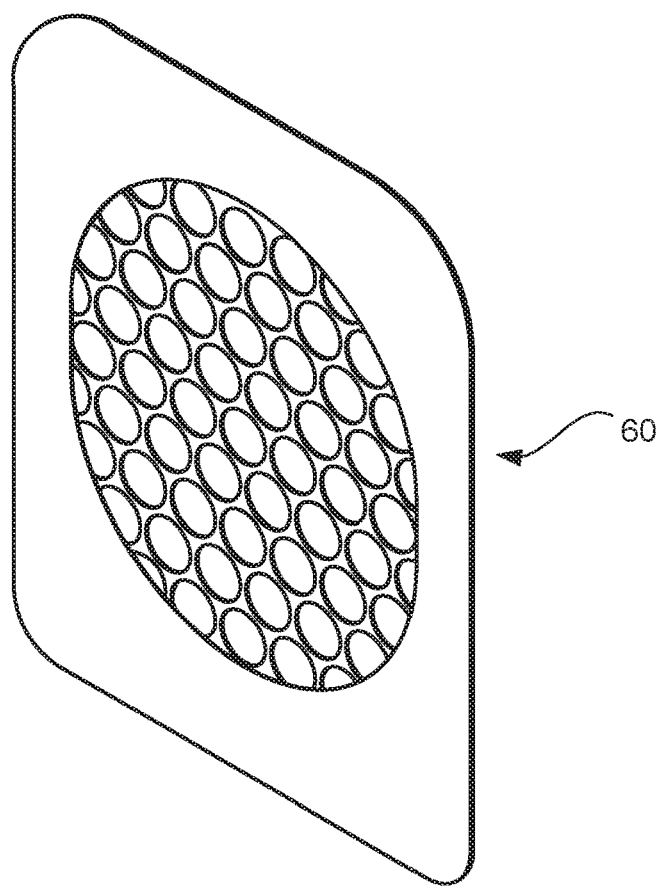
FIG. 6 is a perspective view of a protective film assembly according to the present invention.
Figure 7:
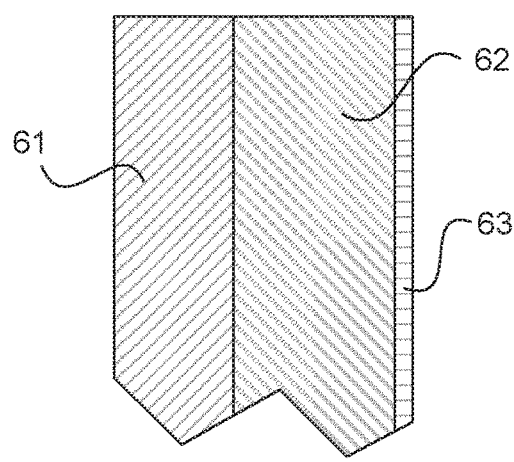
FIG. 7 is an expanded partial cross-section showing the layers of the protective film assembly.

Referring now to FIG. 6, there is shown a perspective view of a film assembly 60, which is an embodiment of protective film 6. FIG. 7 shows an expanded partial cross-section of film assembly 60, and it is seen that film assembly 60 comprises 3 layers, namely a frame 61, an adhesive layer 62 and a thin film 63.

Figure 8C:
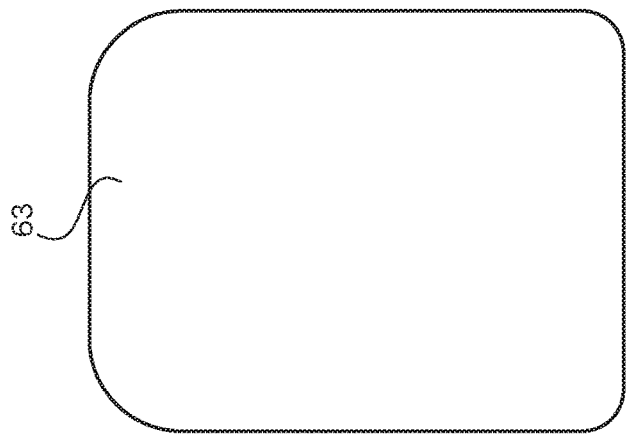
FIGS. 8a, 8b and 8c show separated plan views of each of the layers of the protective film assembly.
Figure 8B:
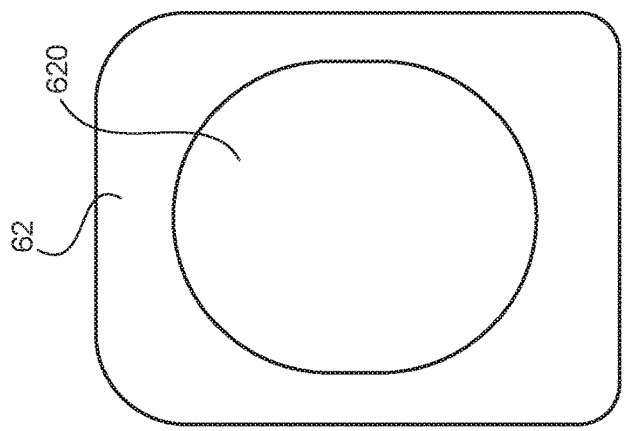
Figure 8A:
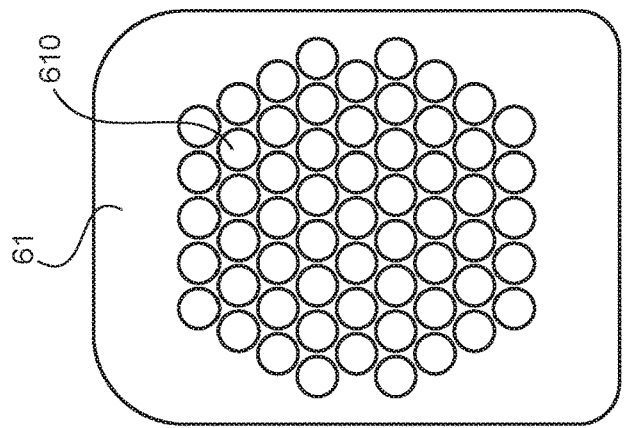

FIG. 8a is a plan view of frame 61 in which an aperture array 610 comprising multiple closely spaced apertures has been formed. Frame 61 is made of a material which is strong enough and thick enough to provide adequate support for thin film 63. In view of its thickness, the material of frame 61 is likely to block some or all of the X-rays, particularly when the X-rays have lower energy.

The individual apertures of aperture array 610 are shown as circular in FIG. 8a, but they may have any suitable shape. The geometrical configuration of the apertures in aperture array 610 as shown in FIG. 8a is for illustrative purposes only. In general, aperture array 610 is configured to achieve the largest aperture area consistent with maintaining the strength and integrity of the material of frame 61 remaining between the individual apertures. Achieving large aperture area enables high X-ray transmission through the apertures, and maintaining strength and integrity of the material of frame 61 ensures adequate support for thin film 63. Any aperture shape or aperture array configuration is within the scope of the present invention.

In an embodiment, frame 61 is made of polyimide (Kapton), and its thickness is between 20 um and 100 um, preferably 76 um. The apertures in frame 61 may be made by means of a steel die, by laser machining, or by any other suitable machining technique.

FIG. 8b is a plan view of adhesive layer 62 into which a single aperture 620 has been formed. The perimeter of aperture 620 corresponds approximately to the outermost perimeter of aperture array 610. Adhesive layer 62 may be made of any adhesive material suitable for affixing thin film 63 to frame 61.

In an embodiment, adhesive layer 62 is made of a double-coated adhesive tape, such as 93010LE tape manufactured by 3M Corporation which has release paper (not shown) on both sides and a thickness of about 90 um after removal of the release paper.

FIG. 8c is a plan view of thin film 63. Thin film 63 may be made of any suitable material and with any suitable thickness for X-ray transmission. In an embodiment, thin film 63 is made of Prolene and has a thickness of between 3 um and 10 um, preferably 6 um. A 6 um Prolene film is suitable for transmission of low energy X-rays, transmitting approximately 35% of X-rays having an energy of 1,000 eV and approximately 85% of X-rays having an energy of 2,000 eV. However, in the absence of the support provided by frame 61, a 6 um Prolene film would be too fragile for use in the X-ray instrument.

Film assembly 60 is assembled by first peeling off the release paper from one side of adhesive layer 62, and then applying adhesive layer 62 to frame 61. The release paper is then removed from the second side of adhesive layer 62 and thin film 63 is attached to complete the assembly.

For cost effective high volume production, multiple copies of film assembly 60 may be produced by attaching three large sheets of material each having arrays of parts as shown in FIGS. 8a, b and c respectively. Arrays may be, for example, 10×10, thereby producing 100 copies per attached sheet. Individual copies of film assembly 60 would then be separated by cutting from the large attached sheet.

An alternative high volume production method uses a continuous roll process in which three ribbons of material each having multiple copies of frame 61, adhesive layer 62 and thin film 63 respectively are laminated together.

Although the present invention has been described in relation to particular embodiments thereof, it can be appreciated that various designs can be conceived based on the teachings of the present disclosure, and all are within the scope of the present disclosure.

What is claimed is:

1. An X-Ray Fluorescence (XRF) test system comprising an XRF test instrument used for testing a test target's responses to X-rays, the instrument including a test window allowing the X-rays and its responsive energy to pass through, a window protecting film assembly allowing the X-rays to pass through and provide protection to the window, wherein the film assembly is configured to be coupled with the window in a fashion to be removable from or attached, or re-attached over the window;
   wherein the film assembly is configured to be removable and reattachably attached over the window by adhesive coupling along or partially along the circumference of the film assembly;
   wherein the film assembly comprises:
      a frame made of a frame material and having an array of frame apertures, the frame apertures being confined within an array perimeter;
      an adhesive layer having an adhesive layer aperture, the perimeter of the adhesive layer aperture corresponding to the array perimeter; and
      a thin film;
   wherein the adhesive layer is disposed between the frame and the thin film.

2. The system of claim 1 wherein the thin film is supported by the frame.

3. The system of claim 1 wherein the frame material is polyimide material having a thickness of between 20 um and 100 um.

4. The system of claim 1 wherein the frame apertures are made by a steel die punching technique.

5. The system of claim 1 wherein the frame apertures are made by a laser machining technique.

6. The system of claim 1 wherein the adhesive layer is a double-coated adhesive tape.

7. The system of claim 1 wherein the thin film is made of Prolene material having a thickness of between 3 um and 10 um.

8. A window protecting film assembly allowing X-rays to pass through and providing protection to a test window of an XRF instrument, the film assembly being applied with an adhesive coupling such that the film assembly is configured to be coupled to the window in a fashion to be removed from, or applied, or re-applied over the window removably and reattachably attached to the window via the adhesive coupling along or partially along the circumference of the film assembly, and wherein the XRF test instrument is used for testing a test target's responses to X-rays;
   wherein the film assembly comprises:
      a frame made of a frame material and having an array of frame apertures, the frame apertures being confined within an array perimeter;
      an adhesive layer having an adhesive layer aperture, the perimeter of the adhesive layer aperture corresponding to the array perimeter; and
      a thin film; and
   wherein the adhesive layer is disposed between the frame and the thin film.

9. The film assembly of claim 8 wherein the thin film is supported by the frame.

10. The film assembly of claim 8 wherein the frame material is polyimide material having a thickness of between 20 um and 100 um.

11. The film assembly of claim 8 wherein the frame apertures are made by a steel die punching technique.

12. The film assembly of claim 8 wherein the frame apertures are made by a laser machining technique.

13. The film assembly of claim 8 wherein the adhesive layer is a double-coated adhesive tape.

14. The film assembly of claim 8 wherein the thin film is made of Prolene material having a thickness of between 3 um and 10 um.

* * * * *